(12) United States Patent
Eldridge et al.

(10) Patent No.: US 10,610,692 B2
(45) Date of Patent: Apr. 7, 2020

(54) ELECTRICAL CONNECTORS FOR IMPLANTABLE DEVICES

(71) Applicant: Thoratec Corporation, Pleasanton, CA (US)

(72) Inventors: David Eldridge, Brentwood, CA (US); Joseph C. Stark, III, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 163 days.

(21) Appl. No.: 14/910,506

(22) PCT Filed: Mar. 6, 2015

(86) PCT No.: PCT/US2015/019174
§ 371 (c)(1),
(2) Date: Feb. 5, 2016

(87) PCT Pub. No.: WO2015/134871
PCT Pub. Date: Sep. 11, 2015

(65) Prior Publication Data
US 2016/0367819 A1    Dec. 22, 2016

Related U.S. Application Data

(60) Provisional application No. 61/949,068, filed on Mar. 6, 2014.

(51) Int. Cl.
*A61N 1/375* (2006.01)
*H02J 50/12* (2016.01)
(Continued)

(52) U.S. Cl.
CPC ......... *A61N 1/3752* (2013.01); *A61N 1/3787* (2013.01); *H01R 13/5224* (2013.01);
(Continued)

(58) Field of Classification Search
CPC .............................. A61M 1/127; H02J 7/025
See application file for complete search history.

(56) References Cited

U.S. PATENT DOCUMENTS

| 4,041,955 | A | 8/1977 | Kelly et al. |
| 4,352,960 | A | 10/1982 | Dormer et al. |

(Continued)

FOREIGN PATENT DOCUMENTS

| DE | 202012000166 U1 | 4/2013 |
| DE | 102012201073 A1 | 7/2013 |

(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

(Continued)

*Primary Examiner* — Michael J D Abreu
(74) *Attorney, Agent, or Firm* — Armstrong Teasdale LLP (57) ABSTRACT

Disclosed are systems for wireless energy transfer including transcutaneous energy transfer. Embodiments are disclosed for electrical connections between an implanted wireless receiver and an implanted medical device powered by the receiver. Methods for manufacturing and using the devices and system are also disclosed.

14 Claims, 6 Drawing Sheets

(51) Int. Cl.
*H01R 13/52* (2006.01)
*H01R 24/58* (2011.01)
*H02J 50/10* (2016.01)
*A61N 1/378* (2006.01)
*H01R 13/187* (2006.01)

(52) U.S. Cl.
CPC .............. *H01R 24/58* (2013.01); *H02J 50/10* (2016.02); *H02J 50/12* (2016.02); *H01R 13/187* (2013.01); *H01R 2201/12* (2013.01)

(56) References Cited

U.S. PATENT DOCUMENTS

| | | | |
|---|---|---|---|
| 4,561,443 A | 12/1985 | Hogrefe et al. | |
| 4,561,444 A | 12/1985 | Livingston et al. | |
| 4,630,615 A | 12/1986 | Yomtov | |
| 4,679,560 A | 7/1987 | Galbraith | |
| 4,726,378 A | 2/1988 | Kaplan | |
| 4,736,747 A | 4/1988 | Drake | |
| 4,924,171 A | 5/1990 | Baba et al. | |
| 4,945,305 A | 7/1990 | Blood | |
| 5,070,223 A | 12/1991 | Colasante | |
| 5,076,270 A * | 12/1991 | Stutz, Jr. ............... | A61N 1/3752 607/37 |
| 5,346,458 A | 9/1994 | Affeld | |
| 5,350,413 A | 9/1994 | Miller et al. | |
| 5,569,156 A | 10/1996 | Mussivand | |
| 5,630,836 A | 5/1997 | Prem et al. | |
| 5,690,693 A | 11/1997 | Wang et al. | |
| 5,702,431 A | 12/1997 | Wang et al. | |
| 5,755,748 A | 5/1998 | Borza | |
| 5,771,438 A | 6/1998 | Palermo et al. | |
| 5,831,248 A | 11/1998 | Hojyo et al. | |
| 5,948,006 A | 9/1999 | Mann | |
| 6,123,726 A | 9/2000 | Mori et al. | |
| 6,149,683 A | 11/2000 | Lancisi et al. | |
| 6,212,430 B1 | 4/2001 | Kung | |
| 6,296,533 B1 | 10/2001 | Grubbs et al. | |
| 6,312,338 B1 | 11/2001 | Sato et al. | |
| 6,320,354 B1 | 11/2001 | Sengupta et al. | |
| 6,324,431 B1 | 11/2001 | Zarinetchi et al. | |
| 6,327,504 B1 | 12/2001 | Dolgin et al. | |
| 6,332,810 B1 * | 12/2001 | Bareel ................ | H01R 13/6464 439/676 |
| 6,389,318 B1 | 5/2002 | Zarinetchi et al. | |
| 6,400,991 B1 | 6/2002 | Kung | |
| 6,442,434 B1 | 8/2002 | Zarinetchi et al. | |
| 6,451,055 B1 | 9/2002 | Weiss | |
| 6,458,164 B1 | 10/2002 | Weiss | |
| 6,478,820 B1 | 11/2002 | Weiss | |
| 6,553,263 B1 | 4/2003 | Meadows et al. | |
| 6,579,315 B1 | 6/2003 | Weiss | |
| 6,591,139 B2 | 7/2003 | Loftin et al. | |
| 6,605,032 B2 | 8/2003 | Benkowski et al. | |
| 6,647,298 B2 | 11/2003 | Abrahamson et al. | |
| 6,650,213 B1 | 11/2003 | Sakurai et al. | |
| 6,723,039 B2 | 4/2004 | French et al. | |
| 6,772,011 B2 | 8/2004 | Dolgin | |
| 6,801,807 B2 | 10/2004 | Abrahamson | |
| 6,810,289 B1 | 10/2004 | Shaquer | |
| 6,850,803 B1 | 2/2005 | Jimenez et al. | |
| 6,894,456 B2 | 5/2005 | Tsukamoto et al. | |
| 6,895,281 B1 | 5/2005 | Amundson et al. | |
| 6,949,065 B2 | 9/2005 | Sporer et al. | |
| 6,960,968 B2 | 11/2005 | Odendaal et al. | |
| 6,967,621 B1 | 11/2005 | Cadotte, Jr. et al. | |
| 6,985,773 B2 | 1/2006 | Von Arx et al. | |
| 7,015,769 B2 | 3/2006 | Schulman et al. | |
| 7,107,103 B2 | 9/2006 | Schulman et al. | |
| 7,126,310 B1 | 10/2006 | Barron | |
| 7,225,032 B2 | 5/2007 | Schmeling et al. | |
| 7,246,040 B2 | 7/2007 | Borg et al. | |
| 7,286,880 B2 | 10/2007 | Olson et al. | |
| 7,299,095 B1 * | 11/2007 | Barlow ................ | A61N 1/3752 607/36 |
| 7,428,438 B2 | 9/2008 | Parramon et al. | |
| 7,471,986 B2 | 12/2008 | Hatlestad | |
| 7,496,733 B2 | 2/2009 | Altman et al. | |
| 7,505,816 B2 | 3/2009 | Schmeling et al. | |
| 7,515,012 B2 | 4/2009 | Schulman et al. | |
| 7,522,878 B2 | 4/2009 | Baarman | |
| 7,532,901 B1 | 5/2009 | Lafranchise et al. | |
| 7,565,187 B1 | 7/2009 | Dynok et al. | |
| 7,571,007 B2 | 8/2009 | Erickson et al. | |
| 7,574,173 B2 | 8/2009 | Terranova et al. | |
| 7,587,241 B2 | 9/2009 | Parramon et al. | |
| 7,599,743 B2 | 10/2009 | Hassler et al. | |
| 7,650,187 B2 | 1/2010 | Gruber et al. | |
| 7,650,192 B2 | 1/2010 | Wahlstrand | |
| 7,711,433 B2 | 5/2010 | Davis et al. | |
| 7,720,546 B2 | 5/2010 | Ginggen et al. | |
| 7,741,734 B2 | 6/2010 | Joannopoulos et al. | |
| 7,761,164 B2 | 7/2010 | Verhoef et al. | |
| 7,774,069 B2 | 8/2010 | Olson et al. | |
| 7,782,190 B1 | 8/2010 | Martin et al. | |
| 7,805,200 B2 | 9/2010 | Kast et al. | |
| 7,812,481 B2 | 10/2010 | Iisaka et al. | |
| 7,818,036 B2 | 10/2010 | Lair et al. | |
| 7,818,037 B2 | 10/2010 | Lair et al. | |
| 7,825,543 B2 | 11/2010 | Karalis et al. | |
| 7,830,114 B2 | 11/2010 | Reed | |
| 7,865,245 B2 | 1/2011 | Torgerson et al. | |
| 7,872,367 B2 | 1/2011 | Recksiek et al. | |
| 7,904,170 B2 | 3/2011 | Harding | |
| 7,932,696 B2 | 4/2011 | Peterson et al. | |
| 7,962,222 B2 | 6/2011 | He et al. | |
| RE42,682 E | 9/2011 | Barreras et al. | |
| 8,076,801 B2 | 12/2011 | Karalis et al. | |
| 8,081,925 B2 | 12/2011 | Parramon et al. | |
| 8,096,954 B2 | 1/2012 | Stahmann et al. | |
| 8,140,168 B2 | 3/2012 | Olson et al. | |
| 8,150,529 B2 | 4/2012 | Snell et al. | |
| 8,165,694 B2 | 4/2012 | Carbunaru et al. | |
| 8,185,212 B2 | 5/2012 | Carbunaru et al. | |
| 8,193,766 B2 | 6/2012 | Rondoni et al. | |
| 8,203,434 B2 | 6/2012 | Yoshida | |
| 8,244,367 B2 | 8/2012 | Wahlstrand et al. | |
| 8,247,926 B2 | 8/2012 | Issa et al. | |
| 8,258,653 B2 | 9/2012 | Kitamura et al. | |
| 8,265,770 B2 | 9/2012 | Toy et al. | |
| 8,278,784 B2 | 10/2012 | Cook et al. | |
| 8,292,052 B2 | 10/2012 | Bohori et al. | |
| 8,299,652 B2 | 10/2012 | Smith et al. | |
| 8,301,079 B2 | 10/2012 | Baarman | |
| 8,319,473 B2 | 11/2012 | Choi et al. | |
| 8,362,742 B2 | 1/2013 | Kallmyer | |
| 8,373,310 B2 | 2/2013 | Baarman et al. | |
| 8,378,522 B2 | 2/2013 | Cook et al. | |
| 8,378,523 B2 | 2/2013 | Cook et al. | |
| 8,463,395 B2 | 6/2013 | Forsell | |
| 8,489,200 B2 | 7/2013 | Zarinetchi et al. | |
| 8,551,163 B2 | 10/2013 | Aber et al. | |
| 8,562,508 B2 | 10/2013 | Dague et al. | |
| 8,581,793 B2 | 11/2013 | Carr | |
| 8,587,154 B2 | 11/2013 | Fells et al. | |
| 8,620,447 B2 | 12/2013 | D'Ambrosio et al. | |
| 8,628,460 B2 | 1/2014 | Yomtov et al. | |
| 8,629,578 B2 | 1/2014 | Kurs et al. | |
| 8,668,473 B2 | 3/2014 | Larose et al. | |
| 8,694,117 B2 | 4/2014 | Aghassian et al. | |
| 8,810,071 B2 | 8/2014 | Sauerlaender et al. | |
| 8,849,415 B2 * | 9/2014 | Bedenbaugh .......... | H01R 4/363 607/115 |
| 8,884,468 B2 | 11/2014 | Lemmens et al. | |
| 8,909,351 B2 | 12/2014 | Dinsmoor et al. | |
| 8,971,958 B2 | 3/2015 | Frikart et al. | |
| 9,002,468 B2 | 4/2015 | Shea et al. | |
| 9,106,083 B2 | 8/2015 | Partovi | |
| 9,192,704 B2 | 11/2015 | Yomtov et al. | |
| 9,302,093 B2 | 4/2016 | Mashiach | |
| 9,515,494 B2 | 12/2016 | Kurs et al. | |
| 9,515,495 B2 | 12/2016 | Kurs et al. | |
| 9,560,787 B2 | 1/2017 | Kallmyer et al. | |
| 2002/0038138 A1 | 3/2002 | Zarinetchi et al. | |

(56) References Cited

U.S. PATENT DOCUMENTS

| | | |
|---|---|---|
| 2002/0087204 A1 | 7/2002 | Kung et al. |
| 2002/0093456 A1 | 7/2002 | Sawamura et al. |
| 2003/0073348 A1* | 4/2003 | Ries .................. A61N 1/3752 439/578 |
| 2003/0171792 A1 | 9/2003 | Zarinetchi et al. |
| 2004/0138725 A1 | 7/2004 | Forsell |
| 2004/0256146 A1 | 12/2004 | Frericks |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0157853 A1* | 6/2015 | Verzal .................. A61N 1/0551 600/25 |
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |

(56) References Cited

U.S. PATENT DOCUMENTS

| | | |
|---|---|---|
| 2016/0250454 A1 | 9/2016 | Beckham |
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089065 | 11/2002 |
| KR | 1020120007296 | 1/2012 |
| KR | 1020120077448 | 7/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Chargepoint, Inc.; −chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988.

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Petersen et al.; U.S. Appl. No. 14/414,840 entitled "Computer Modeling for Resonant Power Transfer Systems," filed Jan. 14, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

\* cited by examiner

ELECTRICAL CONNECTORS FOR IMPLANTABLE DEVICES

CROSS-REFERENCE TO RELATED APPLICATIONS

This application is a National Stage application of International Application No. PCT/US2015/019174, filed Mar. 6, 2015, titled "ELECTRICAL CONNECTORS FOR IMPLANTABLE DEVICES", which claims the benefit of priority to U.S. Provisional Appln. No. 61/949,068, filed Mar. 6, 2014, titled "ELECTRICAL CONNECTORS FOR IMPLANTABLE DEVICES", the contents of which are incorporated by reference herein in their entireties. This application is related to U.S. Provisional Appln. No. 61/794,258, which is incorporated by reference herein in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to reliable electrical connectors for high-powered implantable medical devices in a fluid and tissue saturated environment.

BACKGROUND

Implantable medical devices have been known for many years. Many implanted devices need to transmit and/or receive power or data. Examples of such devices are pacemakers and implantable cardioverter-defibrillators (ICD).

Implanted medical devices often require electrical connectors for transmitting and receiving power. The connectors must be remain stable and operate reliably for many years to avoid the need for operating on the patient to replace the components. Corrosion can be a challenge because such medical devices include metal parts receiving power in a fluid environment.

Pacemaker leads are well known for providing a stable and reliable electrical connection. Over the years pacemaker leads have developed to provide stable electrical connections while resisting corrosion and wear. Examples include U.S. Pub. Nos. 2010/0010604, 2011/0196464, 2010/0010604, and 2013/0109905 and U.S. Pat. Nos. 5,433,744 and 8,583,259, the entire contents of which publications and patents are incorporated herein for all purposes. A problem with existing electrical connectors for medical devices is that they do not remain stable when subjected to higher power and/or more challenging fluid environments.

Connectors for other fluid environments have also been developed. Examples include underwater connectors and the like. Examples include European Pub. No. EP2665135 and EP2665137 and International Pub. No. WO1991/015882, the entire contents of which are incorporated herein for all purposes. A problem with such connectors is that they are designed for a specific fluid environment (e.g., water) and operating conditions.

There is a continuing need for improved electrical connectors for implanted medical devices. More broadly, there is the continuing need for improved reliable connectors for application in fluid-saturated environments, and in various respects body fluids.

SUMMARY

An implantable connector configured to carry power and control signals to a medical device is provided, comprising a female connector comprising a jack, one or more wiper seals disposed in the jack, one or more cantilevered electrical spring contacts disposed in the jack and positioned adjacent to or surrounded by the one or more wiper seals, and a male connector comprising, a plug adapted to be inserted into the jack of the female connector, one or more electrical contacts disposed on the plug, the one or more electrical contacts configured to be electrically coupled to the one or more cantilevered electrical spring contacts and wiped clean of bodily fluid and/or debris when the plug of the male connector is inserted into the jack of the female connector.

In some embodiments, the cantilevered electrical spring contacts comprise platinum iridium.

A wirelessly powered implantable system is provided, comprising an implantable module adapted to be implanted within a patient and to receive wireless energy from an external module, a medical device adapted to be implanted within the patient and to receive power and control signals from the implantable module via a driveline cable, and a bulkhead connector configured to connect the driveline cable to the implantable module, the bulkhead connector comprising a female connector including a jack, one or more wiper seals disposed in the jack, and one or more cantilevered electrical spring contacts disposed in the jack and positioned adjacent to or surrounded by the one or more wiper seals, and a male connector including a plug adapted to be inserted into the jack of the female connector and one or more electrical contacts disposed on the plug, the one or more electrical contacts configured to be electrically coupled to the one or more cantilevered electrical spring contacts and wiped clean of bodily fluid and/or debris, when the plug of the male connector is inserted into the jack of the female connector.

In some embodiments, the cantilevered electrical spring contacts comprise platinum iridium.

A method of providing an electrical connection in an implantable system is provided, comprising inserting a plug of a male connector into a jack of a female connector, wiping the plug with wiper seals disposed in the jack to clean the plug of bodily fluid and/or debris, and placing one or more platinum iridium cantilevered electrical spring contacts of the female connector into contact with electrical contacts of the male connector to electrically couple the female connector to the male connector.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Figure 1:
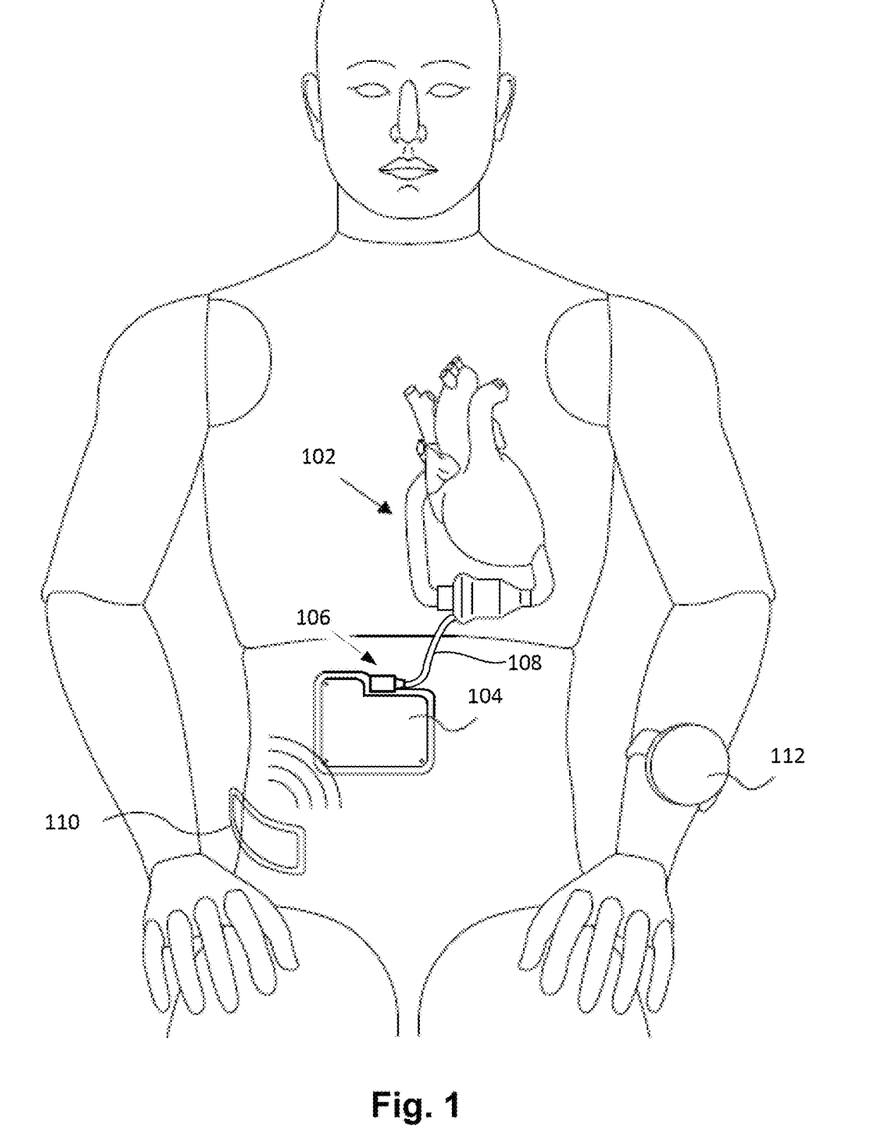
FIG. 1 shows an implantable system with an electrical connector comprising a bulkhead connector and a driveline cable.

FIG. 1 shows an implantable medical system 100 that includes an implantable medical device 102 (shown as a ventricular assist device) and an implanted module 104 configured to receive wireless power from outside the body to provide power and control signals for the medical device. A bulkhead connector 106 and driveline cable 108 connect the implanted module to the medical device to provide power, data, and or/control signals from the module to the device. In one embodiment, the medical device is a relatively high powered device. In some embodiments the module supplies average power of about 5 VAC, about 10 VAC, or about 15 VAC. In some embodiments the module supplies peak power of 5 VAC, 10 VAC, 15 VAC, or 25 VAC. In one embodiment, the implanted module is configured to remain inside the patient's body for a minimum of three years, and to serve as the power source and controller for the medical device. In an exemplary embodiment the module is configured to supply ~16 VAC to drive the medical device.

In another embodiment, the implanted module 104 can include a receiver resonator coil and electronics configured to receive wireless energy from an external transmitter 110, which can include a power supply such as a pulse generator connected to a transmitter resonator coil. The connector can allow a clinician to surgically replace the implanted module by disconnecting the existing driveline cable from the existing module, removing the existing module, and reconnecting the same driveline cable to a new module without removing the medical device. Similarly, the clinician can surgically replace the cable and/or the medical device while leaving the implanted module in place. In some embodiments, an external user interface 112 can be configured to communicate with the implanted module 104 and can be worn by the patient, such as on the patient's wrist. In other embodiments, the external controller can be an electronic computing device such as a personal computer, a tablet, smartphone, or laptop computer.

Figure 2:
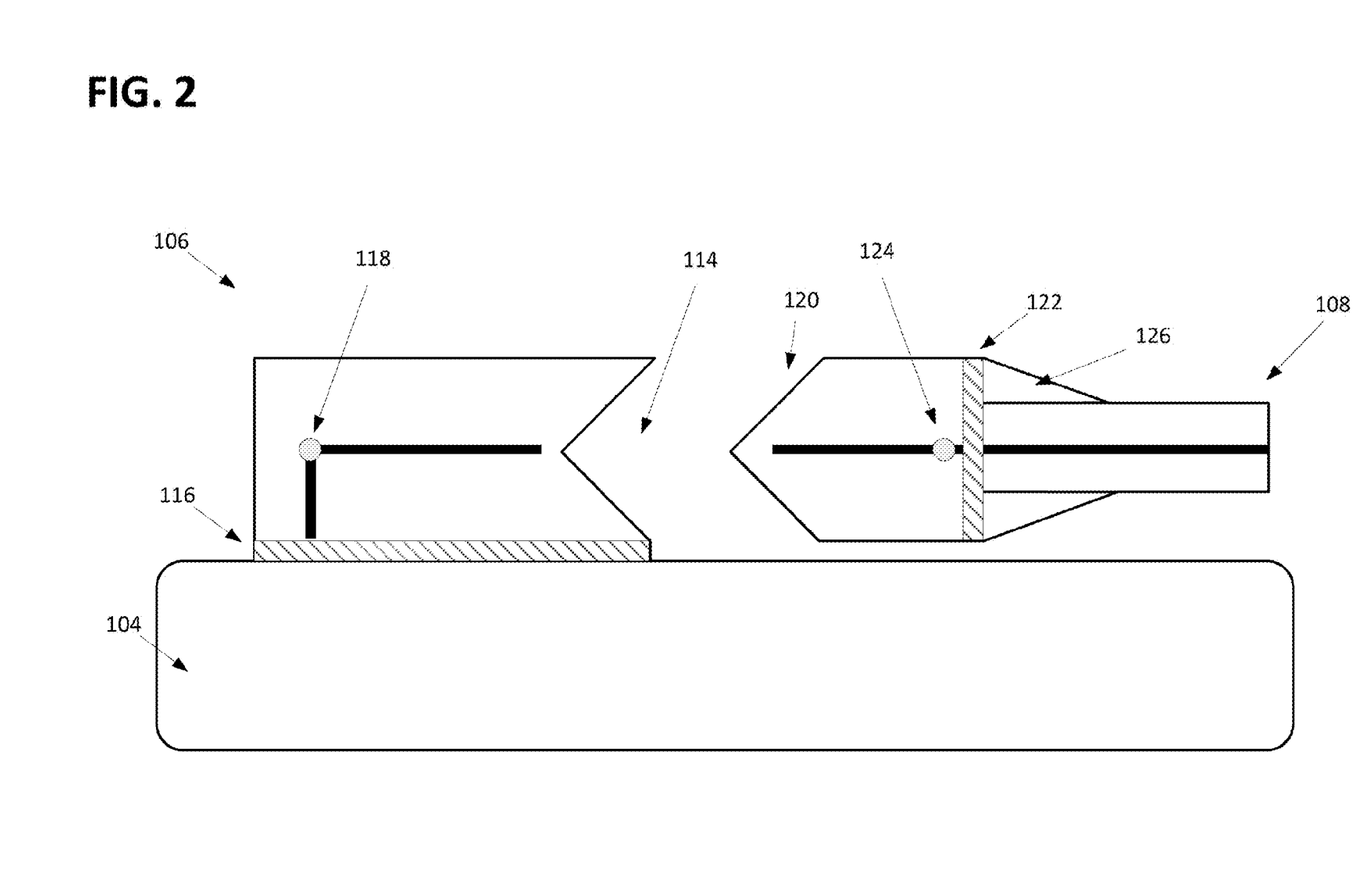
FIG. 2 is a schematic drawing of the connector.

FIG. 2 is a schematic drawing showing an interface between a bulkhead connector 106 and a driveline cable 108. The bulkhead connector can include a female connector 114, a mechanical interface 116 connecting the female connector to the implanted module 104, and an electrical interface 118. The driveline cable 108 can include a male connector 120, a mechanical interface 122, an electrical interface 124, and a strain relief 126 on the driveline cable at the male connector end. The mechanical interface between the female connector and the implanted module and between the male connector and the driveline cable can comprise an adhesive, for example an epoxy. It should be understood that in other embodiments, the bulkhead connector can include a male connector and the driveline cable can comprise a female connector.

Various aspects of the bulkhead connector are similar to those shown and described in U.S. Pat. Nos. 4,655,462, 4,826,144, 4,876,781, 4,907,788, 4,915,366, 4,961,253, 4,964,204, 5,139,243, 5,160,122, 5,503,375, 5,615,870, 5,709,371, 5,791,638, 7,055,812, 4,678,210, 5,082,390, 5,411,348, 5,545,842, 6,749,358, 6,835,084, 7,070,455, and 7,195,523, the entire contents of which are incorporated herein for all purposes by reference.

Figure 3A:
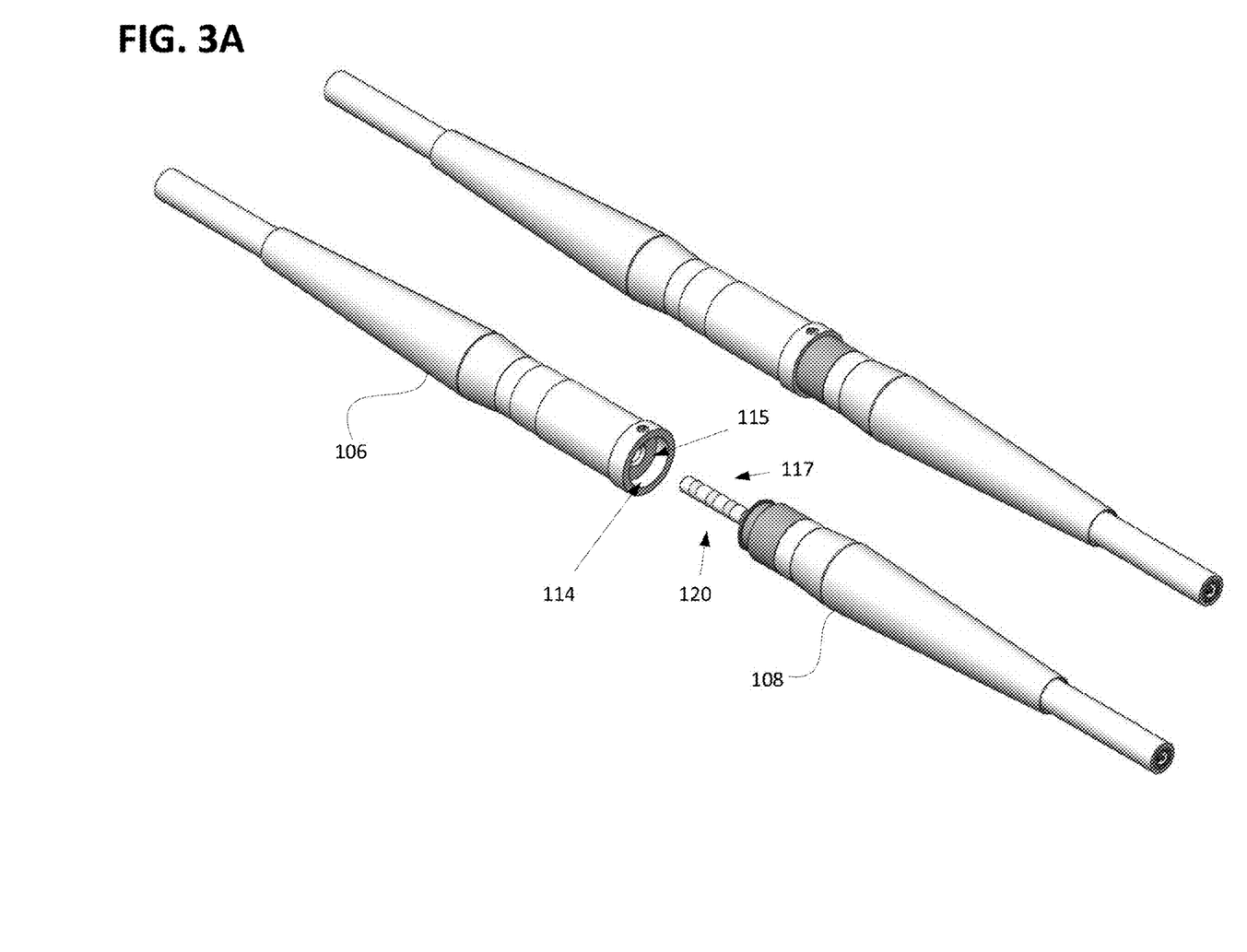
FIGS. 3A-3D show various views of an electrical connector.

FIG. 3A shows an embodiment of a connector including a connector 106 with a female connector 114 and a driveline cable 108 with a male connector 120. As shown, the female connector 114 can comprise a jack 115 or slot within which the male plug 117 can be inserted to make the electrical connection between the female and male connector. As shown in the embodiment of FIG. 3A, the male connector comprises a single plug and the female connector comprises a single jack, but it should be understood that other embodiments can include any number of a plurality of jacks and plugs. The connector is shown in FIG. 3A both connected (top) and disconnected (bottom). As should be understood, the bulkhead connector 106 can connect to the implantable module 104 of FIG. 1, and the driveline cable can connect to the medical device 102 of FIG. 1, or vice versa.

Figure 3B:
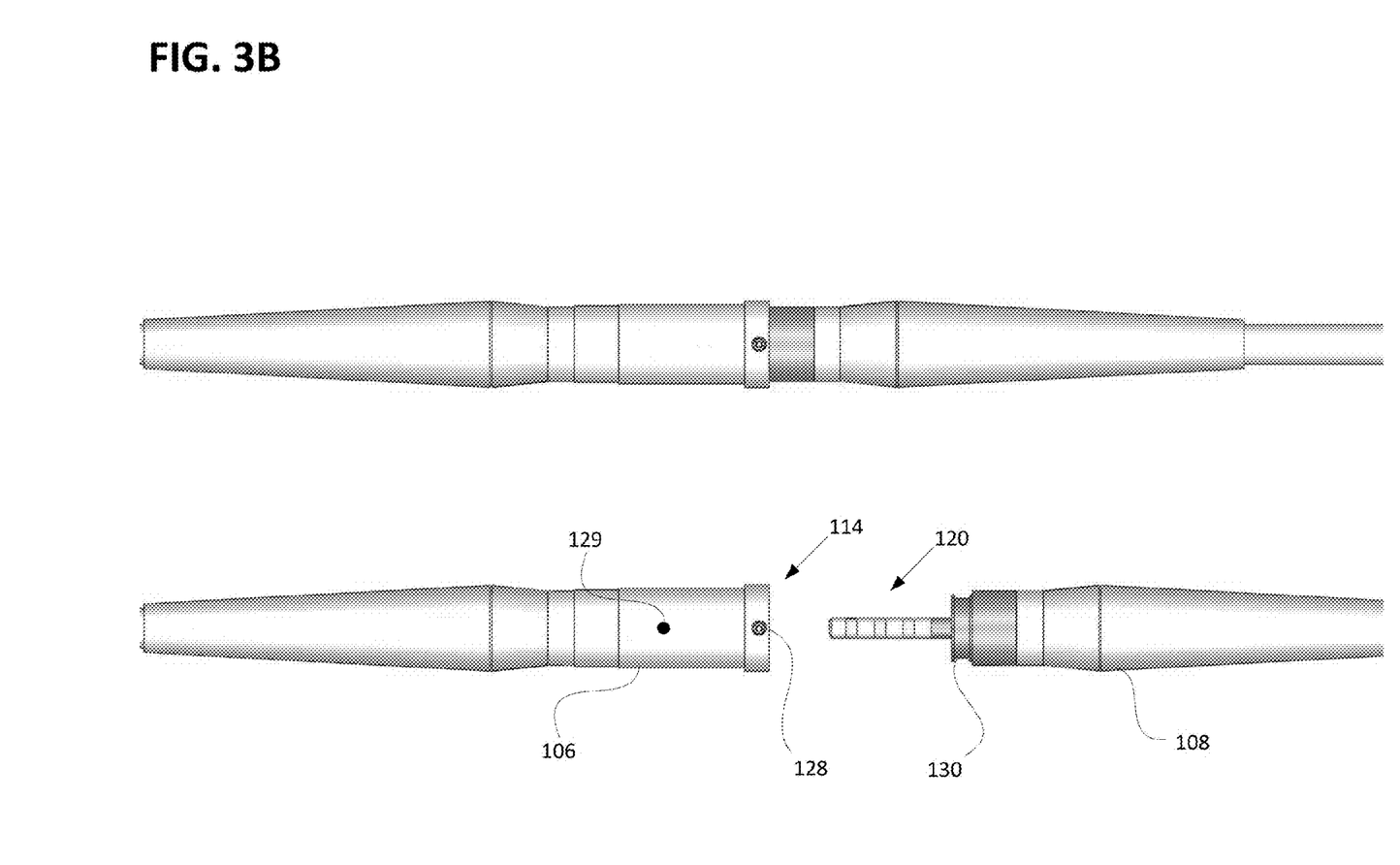

FIG. 3B is another view of the connector of FIG. 3A, showing the connector 106 and the driveline cable 108 from a side view. The bulkhead connector 106 can include a female connector 114 and a set locking screw 128, and the driveline cable 108 can include a male connector 120 and a set screw locking groove 130. As in FIG. 3A, the connection is shown connected in the top of FIG. 3B and disconnected in the bottom of FIG. 3B. In one embodiment, hydrostatic lock between the male and female connectors can be avoided by including a vent 129 in the connector, such as in the female connector, to release excess fluid or pressure when the connection is made. The vent can comprise a passive-one way valve, for example.

Figure 3C:
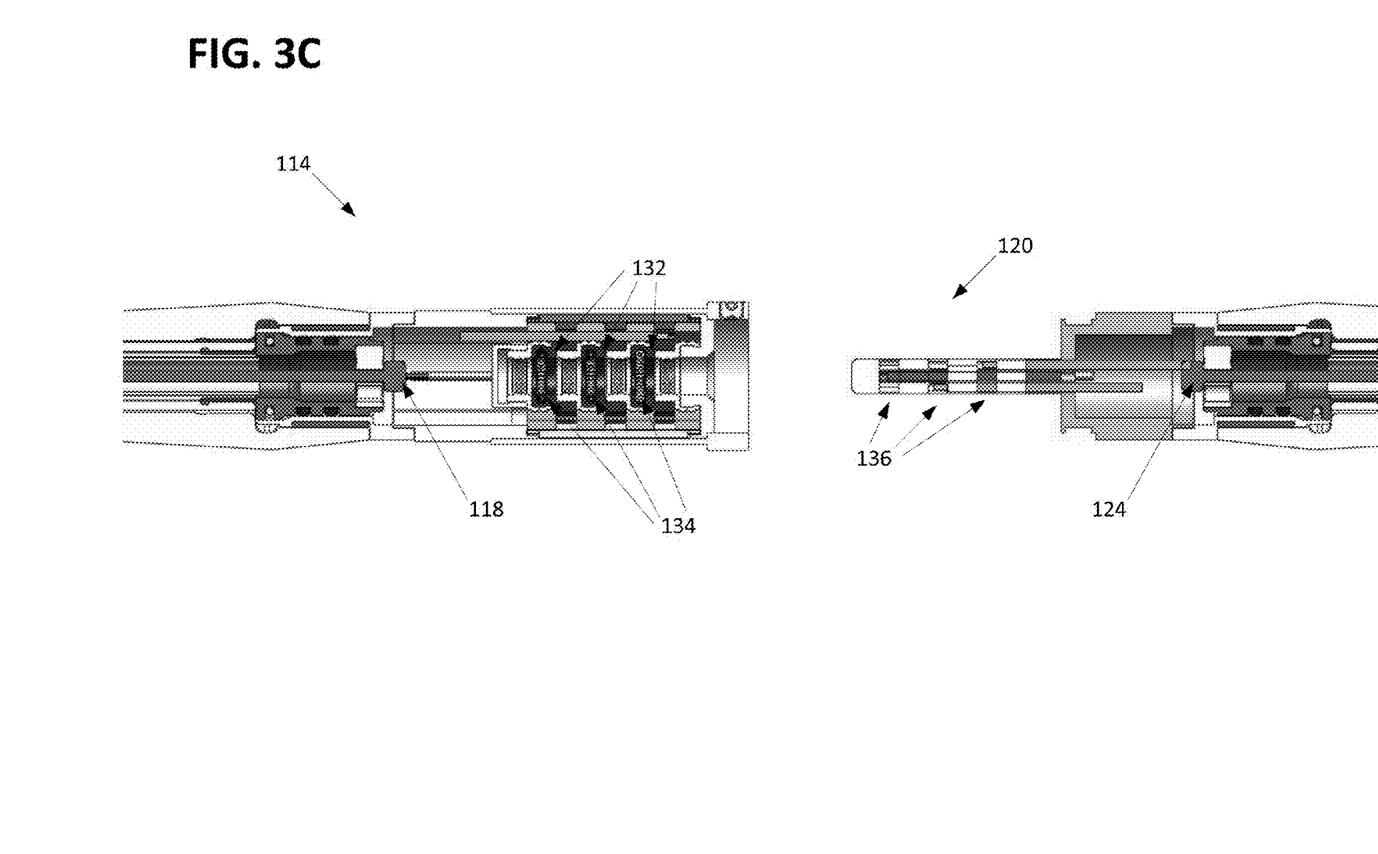

FIG. 3C shows a cutaway view of the connector of FIGS. 3A-4B in the disconnected configuration. The female connector can include one or more o-rings 132 disposed within the jack of the female connector 114 that either surround or are positioned on both sides of the female electrical contacts 134 also disposed within the jack. In some embodiments, other fluid-sealing mechanisms may be employed in lieu of, or in addition to, the o-rings. The o-rings 132 surrounding male electrical contacts 134 can be implemented as wiper seals, as shown in FIG. 3C. The contacts and o-rings are configured to form an interference fit with male electrical contacts 136 on the plug of the male connector 120 to be inserted.

The o-rings acting as wiper seals are configured to perform two functions: they "wipe" the male connector of fluid, debris, and/or bodily fluids during insertion, and also electrically isolate the electrical connection between the female and the male electrical contacts when the male connector is fully inserted into the female connector. In FIG. 3C, the female connector is shown having three female electrical contacts 134, which are configured to couple to three male electrical contacts 136 when the male connector 120 is inserted into the female connector 114. Electrical interfaces 118 and 124 can then carry power and control signals through the female connector 114 and male connector 120, respectively.

Figure 3D:
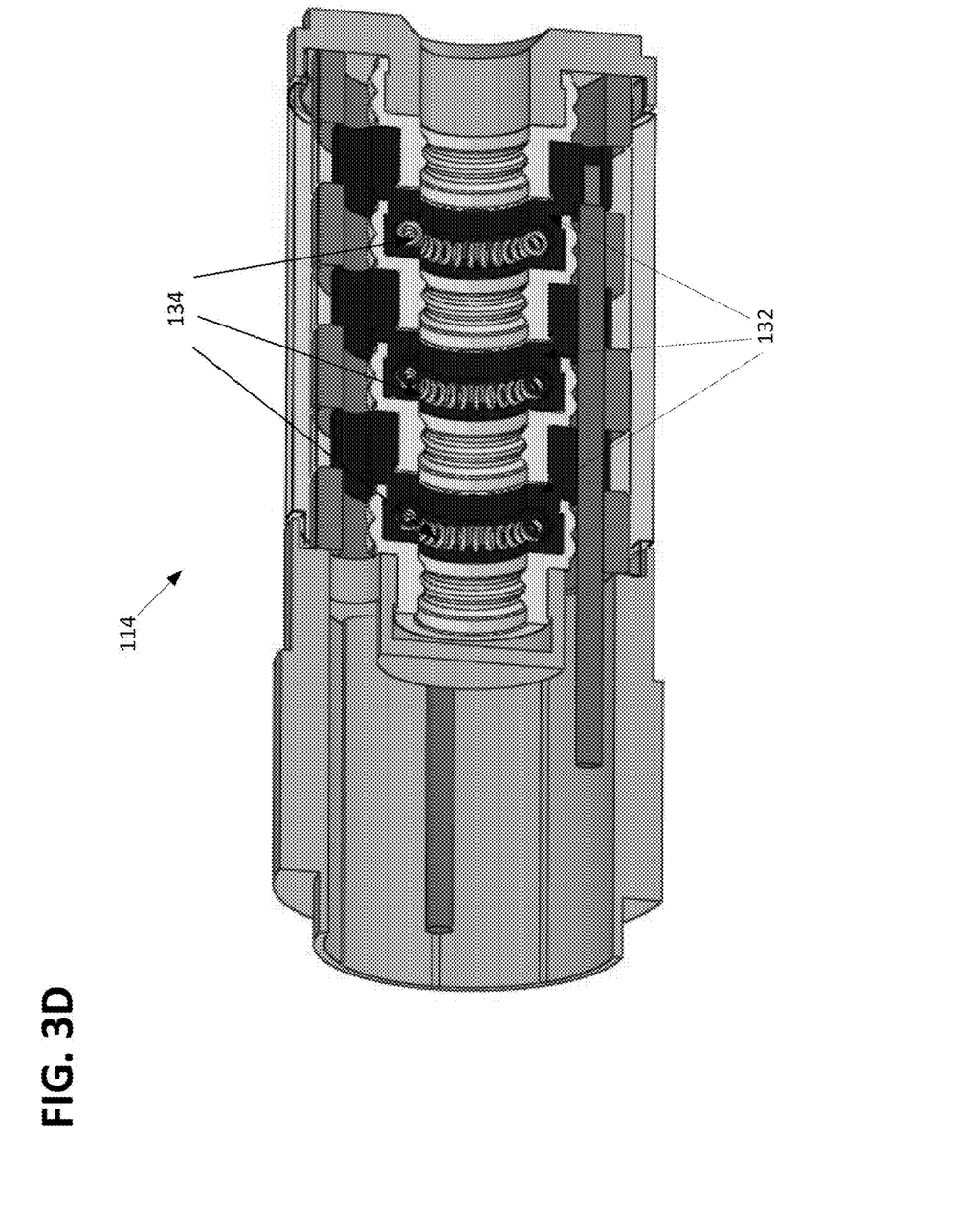

FIG. 3D shows a close-up view of the o-rings 132 and female electrical contacts 134 of the female connector 114.

The female electrical contacts can comprise "canted" or cantilevered springs, as shown, which allows for movement of the female electrical contacts as they engage their corresponding male electrical contacts. An example of a canted spring for an electrical connector is shown and described in U.S. Pub. No. 2012/0174398, the entire contents of which is incorporated herein for all purposes by reference.

In a preferred embodiment, the female electrical contacts, in the form of cantilevered springs, can comprise platinum iridium alloy (Pt-Ir). Platinum iridium has been chosen for its high corrosion resistance. This is particularly important for implanted devices because, in the exemplary embodiment, the connector is saturated in blood and bodily fluids when disconnected inside the body. Although Pt-Ir exemplifies excellent corrosion resistance, its mechanical properties and poor manufacturability make it unsuitable for connector applications. This is particularly true for spring-like elements as described here. By contrast, conventional medical devices typically use other materials which are easier to manufacture. For example, pacemakers typically use MP35N for connectors which can be resistance welded to the wire. These materials are sufficient when exposed to most bodily fluids but have insufficient resistance when saturated in blood for long periods. These materials typically will corrode and fail when exposed to continuous voltages from a high voltage implanted medical device. Pacemakers are typically placed subcutaneously in a pacemaker pocket in the upper torso in part to limit exposure to stresses and strains. The pacemaker location is also relatively easy to access for component replacement. By contrast, the exemplary embodiment illustrates a connector placed deep in the abdominal area where the connector is exposed to high pull forces and stresses. This application is far more demanding than the typical medical application. In addition to the anatomical differences, the high power run through the exemplary connector (e.g., several watts or more of continuous power) further increases the risk of corrosion compared to conventional devices like pacemaker leads.

In one specific embodiment, the cantilevered spring female electrical contacts can have a non-uniform cross-section, where the cantilever is thickest at the point where the contact anchors to the female connector and thins towards the tip of the spring, so deflection is observed towards the tip. The cross section of the female electrical contact can be rectangular or circular, for example. The wiper seals can comprise an electrically isolating material designed to isolate the contacts 419 of the female connector. The wiper seals can be configured to scrape, wipe, or remove fluid or other debris from the male connector as it is inserted into the female connector. One will appreciate from the foregoing that the above configuration provides double sealing. The o-rings isolate individual electrical contacts from the others. In addition, the wiper seals also provide isolation. In this manner a secure and isolated connection is formed with each contact.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implantable connector configured to carry power and control signals to a medical device, comprising:
    a female connector comprising:
        a jack;
        one or more wiper seals disposed in the jack; and
        one or more cantilevered electrical spring contacts disposed in the jack and surrounded by the one or more wiper seals, wherein each of the one or more cantilevered electrical spring contacts is positioned in a groove defined in a respective wiper seal of the one or more wiper seals; and
    a male connector comprising:
        a plug adapted to be inserted into the jack of the female connector; and
        one or more electrical contacts disposed on the plug, the one or more electrical contacts configured to be electrically coupled to the one or more cantilevered electrical spring contacts and wiped clean of bodily fluid by the one or more wiper seals when the plug of the male connector is inserted into the jack of the female connector.

2. The connector of claim 1 wherein the female connector further comprises a vent.

3. The connector of claim 2 wherein the vent comprises a passive one-way valve.

4. The connector of claim 1 wherein the one or more cantilevered electrical spring contacts each have a non-uniform cross-section.

5. The connector of claim 4 wherein each of the one or more cantilevered electrical spring contacts extends from an anchor end to a tip end, and wherein a first cross-section at the anchor end is larger than a second cross-section at the tip end.

6. The connector of claim 1 wherein the cantilevered electrical spring contacts comprise platinum iridium.

7. The connector of claim 1 wherein the female connector is formed on a bulkhead connector.

8. The connector of claim 1 wherein the male connector is formed on a driveline cable.

9. The connector of claim 1 wherein the one or more cantilevered electrical spring contacts comprise three electrical spring contacts.

10. The connector of claim 1 wherein the one or more electrical contacts disposed on the plug comprise three electrical contacts.

11. The connector of claim 1, wherein the male connector further comprises a strain relief.

12. The connector of claim 1, wherein the female connector further comprises a set locking screw.

13. The connector of claim 12, wherein the male connector further comprises a set screw locking groove configured to engage the set locking screw.

14. The connector of claim 1 wherein the each of the one or more wiper seals comprises an o-ring.

* * * * *